(12) United States Patent
Gorsky et al.

(10) Patent No.: US 7,555,144 B2
(45) Date of Patent: Jun. 30, 2009

(54) OPTICAL SCANNING DEVICE FOR LIQUID BIOLOGICAL SAMPLES, PROCESS OF OPERATION AND COMPUTER PROGRAM FOR A COMPUTER CONNECTED TO SAID DEVICE

(75) Inventors: Gabriel Gorsky, Villefranche sur Mer (FR); Marc Picheral, Nice (FR); Philippe Grosjean, Nice (FR)

(73) Assignees: Centre National de la Recherche Scientifique (CNRS), Paris (FR); Universite Pierre et Marie Curie (Paris VI), Paris (FR)

( * ) Notice: Subject to any disclaimer, the term of this patent is extended or adjusted under 35 U.S.C. 154(b) by 1324 days.

(21) Appl. No.: 10/725,504

(22) Filed: Dec. 3, 2003

(65) Prior Publication Data

US 2005/0123174 A1    Jun. 9, 2005

(51) Int. Cl.
*G06K 9/00*    (2006.01)

(52) U.S. Cl. .................. 382/110; 382/100; 205/777.5; 205/779; 422/100; 422/58; 422/107

(58) Field of Classification Search ................ 382/100, 382/110; 205/777.5, 779; 422/100, 58, 107; 435/25, 287.1, 287.2
See application file for complete search history.

(56) References Cited

U.S. PATENT DOCUMENTS

| | | | | |
|---|---|---|---|---|
| 5,118,608 | A | * | 6/1992 | Layton et al. ............. 435/7.1 |
| 5,271,902 | A | * | 12/1993 | Sakka et al. ............. 422/100 |
| 5,846,395 | A | * | 12/1998 | Sarrine et al. ............ 204/461 |
| 6,959,618 | B1 | * | 11/2005 | Larsen ..................... 73/865.5 |
| 2001/0035349 | A1 | * | 11/2001 | Matsumoto et al. ...... 204/403 |

* cited by examiner

*Primary Examiner*—Matthew C Bella
*Assistant Examiner*—Ali Bayat
(74) *Attorney, Agent, or Firm*—Young & Thompson

(57) ABSTRACT

Optical scanning device for the production of a 2D computer image of a liquid or humid biological sample observed by transparency, wherein an even thickness of the liquid biological sample is disposed in a tank optically enclosed between an illumination assembly and an optical sensing assembly, the optical sensing assembly having a moving part able to move in a plane parallel to the sample as to scan an area of the sample of sensibly equal thickness, the illumination assembly having a luminous source sensibly homogeneous at least in the scanned area and including towards the sample, an optical grid filter with a surface parallel to the plane and transmitting only light rays sensibly perpendicular to its surface. The sample can be observed by reflection. The tank is open and joint to the optical sensing assembly.

21 Claims, 7 Drawing Sheets

A-A

B-B

Figure 1:
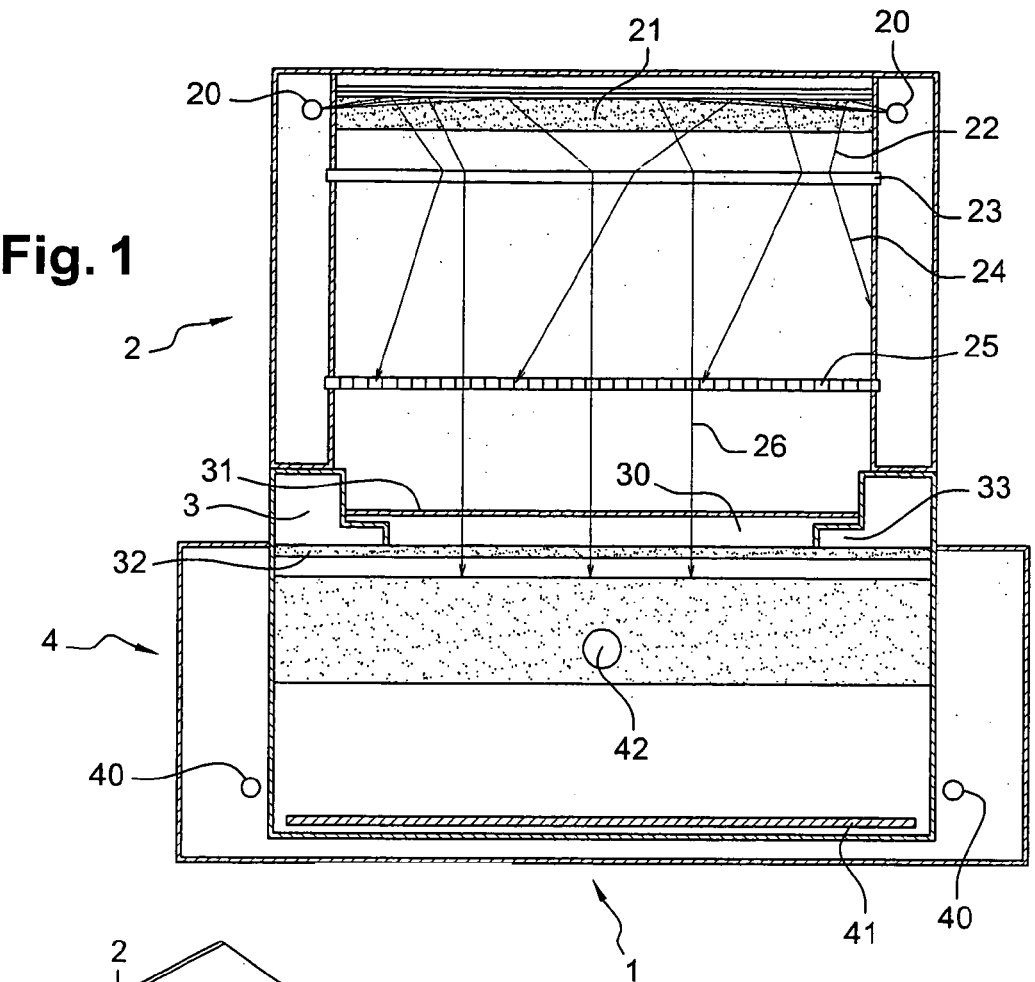

OPTICAL SCANNING DEVICE FOR LIQUID BIOLOGICAL SAMPLES, PROCESS OF OPERATION AND COMPUTER PROGRAM FOR A COMPUTER CONNECTED TO SAID DEVICE

BACKGROUND OF THE INVENTION

The invention is about an optical scanning device for liquid biological samples and a process of operation and also a computer program for a computer connected to said device.

DESCRIPTION OF THE RELATED ART

In seas, zooplanktonic fauna are the main source of energy from the primary producers to higher trophic levels. Their diversity and abundance can influence the population dynamics of most of the commercial fish species. In order to understand and to model population dynamics of zooplankton and fishes with respect to different environmental parameters, a continuous sampling effort by international and national programs is needed. One of the most common sampling methods is the traditional collection of planktonic fauna with nets. One of drawbacks of this method is the time required for sample treatment, that is the identification, enumeration and measurement of individual zooplankton. The process is both time consuming and labor intensive.

A device and a process for improving the treatment of liquid samples with biological objects are thus requested. It has been proposed to use imaging techniques and in the seventies, photographs of the plankton silhouettes were processed in computers. However, this required some manipulations of the sample and the resolution of the processed images was limited. The gain provided with such methods was in fact limited compared to traditional manual techniques.

SUMMARY OF THE INVENTION

The current invention is about an optical scanning device which is simple, low-cost and easy to use for producing images of biological liquid samples and is also about a computerized system including the device and which has means to control said device and for managing the produced images. As such, the invention is also dealing with operating process and computer program.

Firstly, the invention is an optical scanning device for the production of a 2D computer image of an illuminated liquid or humid biological sample observed by transparency.

According to the invention:
- an even thickness of the liquid biological sample is disposed in a tank optically enclosed (i.e. no external light ray may reach the sample or the optical sensing assembly) between an illumination assembly and an optical sensing assembly,
- the optical sensing assembly having a moving part able to move in a plane parallel to the sample as to scan an area of the sample of sensibly equal thickness,
- the illumination assembly having a luminous source sensibly homogeneous in the scanned area and including towards the sample, an optical grid filter with a surface parallel to the plane and transmitting only light rays sensibly perpendicular to its surface.

Following means which may be used alone or in all their possible technical combinations with the invention, are considered:
- the biological sample can, in addition, be observed by reflection, the optical sensing assembly having, in addition, opposite to the sample as regard the moving part, a black end and a lighting assembly, as to allow illumination of the sample from the illumination assembly or from the optical sensing assembly or from both,
- the luminous source of the illumination assembly is a flat lamp,
- the luminous source is an OSRAM® PLANON® lamp,
- the luminous source of the illumination assembly includes a source of light rays emitting light rays towards a luminescent plate disposed parallel to the plane, light rays re-emitted by the luminescent plate towards the sample passing through a frosted plate parallel to the plane before being filtered by the optical grid filter and then reaching the sample,
- the luminescent plate is made of plastic or glass,
- the frosted plate is made of plastic or glass,
- the source of light rays is at least one fluorescent tube,
- the fluorescent tube(s) is (are) lateral to the luminescent plate,
- the fluorescent tube(s) is (are) above the luminescent plate,
- the lighting assembly of the optical sensing assembly is an OSRAM® PLANON® lamp,
- the lighting assembly of the optical sensing assembly has lateral stationary fluorescent tubes,
- the lighting assembly of the optical sensing assembly has a moving fluorescent tube attached to the moving part of the optical sensing assembly,
- the optical sensing assembly is an optical sensor which is a single optical transducer movable along two perpendicular directions in the plane as to scan the area,
- the moving part of the optical sensing assembly is an optical sensor that is a linear sensor having a plurality of unitary optical transducers disposed along a sensing line in the plane, the optical sensor being movable in a direction perpendicular to the sensing line in the plane as to scan the area,
- the moving part of the optical sensing assembly is an optical sensor which is a 2D array sensor having a plurality of unitary optical transducers disposed along a sensing surface parallel to the plane, the optical sensor being movable in the plane as to scan the area,
- the moving part of the optical sensing assembly is a linear mirror disposed along a mirror line in the plane, the linear mirror being movable in a direction perpendicular to the mirror line in the plane as to scan the area and reflecting said area to a fixed optical sensor,
- the fixed optical sensor is a linear array of optical transducers,
- the fixed optical sensor is a 2D array of optical transducers,
- the 2D array of optical transducers (mobile or fixed) is a coupled charge device,
- the sample tank has commanded vibrating means intended to homogenize the sample before scanning,
- the sample tank is a closed chamber having at least one port, two opposite walls parallel to the plane and peripheral walls, at least said two opposite walls being transparent,
- the closed chamber has an input port for introducing the sample (and possibly washing liquid) and an output port for draining,
- the introduction of liquid and the draining are forced through a fluidic circuit having at least a pump,
- the optical scanning device with the closed chamber is useable on any position of the chamber, the chamber being completely filled with the sample, the sample tank is an open chamber with a sample free surface and having a bottom wall parallel to the plane and peripheral walls, at least said bottom wall being transparent, the peripheral walls are stepped by mean of a material to allow the sample to overstep said step in order to avoid a possible meniscus in the image area, the material of the step is transparent, the peripheral walls are stepped by mean of a transparent material to allow the sample to overstep said step in order to avoid a possible meniscus in the image area, the peripheral walls are opaque, the peripheral walls are transparent, preferably, the step of each peripheral wall is transparent and the remaining of the peripheral walls opaque, the steps are integral to the peripheral walls, the steps and the peripheral walls are independent parts, the steps being in the form of stepped walls, the stepped walls are disposed concentrically to the peripheral walls, at least one of the peripheral walls has a gutter, (this acts as an over-fill security if too much sample is introduced in the tank and also as a flush way)

the optical resolution of the device is approximately 10 µm (i.e. a pixel of the image correspond to an area of the sample of about 10 µm in side), the optical scanning device has a magnifier as to have an image of the sample that is enlarged, the optical resolution of the device is less than 10 µm, the illumination assembly is under the sample tank and the optical sensing assembly is above the sample tank, said sample tank being an open chamber joint to the illumination assembly and having peripheral walls and a transparent bottom wall parallel to the plane which is horizontal, and in that the optical sensing assembly is tiltable along one of its edge as to open the device and gain access to the sample tank and, conversely, to close it, the illumination assembly is above the sample tank and the optical sensing assembly is under the sample tank, said sample tank being an open chamber joint to the optical sensing assembly and having peripheral walls and a transparent bottom wall parallel to the plane which is horizontal, and in that the illumination assembly is tiltable along one of its edge as to open the device and gain access to the sample tank and, conversely, to close it, the optical sensing assembly is tiltably supported by a support as to incline the plane from a position where it is horizontal, to a position where it is inclined as to drain the sample tank and, conversely, to return to an horizontal position of the plane, a gutter is provided on the upper surface of at least one peripheral wall of the tank, in case of steps integral to the peripheral walls, the peripheral walls have two steps, the first one overstepped by the sample as to avoid a possible meniscus and a second one at the level of the gutter bottom as to provide an overflow along all peripheral walls, the stepped walls have (totally or partly) a height lower than the height of the peripheral walls, the stepped walls have (totally or partly) a height lower than the height of the bottom of the gutter, the illumination assembly and the optical sensing assembly are interlocked as to allow the draining of the sample tank only when the device is open, the illumination assembly is tiltable along one of its edge over the optical sensing assembly, the illumination assembly is tiltable along one of its edge over the support, the optical scanning device has a control button operated by an operator as to start the scanning, the optical scanning device has a control button operated by the tilting of the illumination assembly, the closure starting scanning and the opening stopping an eventually ongoing scanning.

Secondly, the invention is about a process of operation of an optical scanning device for the production of a 2D computer image of an illuminated liquid or humid biological sample observed by transparency or by reflection.

According to the process of the invention, the optical scanning device is according to any one of previous means alone or in combination and:

in a preparation phase, the device being open, a sample is introduced in the tank, in a scanning phase, the device being closed, the sample is scanned as to produce data corresponding to an image of the sample, in a flushing phase, the device being open, the optical sensing assembly is tilted as to drain the sample tank.

Following means which may be used alone or in all their possible technical combinations with the invention, are considered for the process:

during the scanning phase, in order to illuminate the liquid or humid biological sample, either or both the luminous source of the illumination assembly and the lighting assembly of the optical sensing assembly are switched on, in addition, after draining the tank in the flushing phase, the tank is washed, the process has an additional initializing phase in which a sample which is a pure liquid, notably water, is scanned in order to have data of an image obtained with the pure liquid and is compared to a uniform virtual image and a difference between the images calculated, the calculated difference being used for correcting images of further sample scannings, the reference image for calculating the difference being used for correcting images of further sample scannings is a virtual calculated image, the comparison and calculation is done in the optical scanning device, the correction is done in the optical scanning device, the optical scanning device is connected to a computer, the comparison and calculation is done in the computer, the correction is done in the computer, Thirdly, the invention is about a computer program for the operation of an optical scanning device when said device is connected to said computer.

According to the invention, the optical scanning device is according to any one of previous means alone or in combination and it has means for controlling the device and analyzing the image received from the device into the computer, the means for analyzing being at least one chosen from at least:

an image displaying sub-process, an image contrast correction sub-process, an image luminosity correction sub-process, an image color correction sub-process, an image color to gray or black/white conversion sub-process, an image gray to false color conversion sub-process, an image median filter as to reduce and/or remove isolated artifact pixels in the image, a threshold object(s) selection (organisms of the sample) in the image sub-process, at least one calculation sub-process of attributes of object chosen from at least: surface, length, width, main axles, minimum Ferret diameter, maximum Ferret diameter, mean Ferret diameter, perimeter, convex perimeter, two different measures of elongation, density, roughness, number of holes, binary centroids position, gray level along a determined direction (X, Y, length, width, selected direction), moment (global or along X1Y1, X0Y2, X2Y0) as binary or gray level, angle between the first two main axles, mean and minimum and maximum of value of the gray level, sum of the of the square of gray level, display and storage/retrieval of calculated attributes in association with at least object localization and image reference data, an image selection of objects according to at least one-dimensional parameter, an image selection of part or entirety of the image sub-process, a marking (encircling, squaring, highlighting and or specific color attribution) of the selection, a cutting or pasting sub-process for a selection, an image associated context information display and entry/correction, an image retrieval and storage sub-process with possible associated context information.

The invention is thus based on a low-cost imaging system, designed at the LOV, CNRS-INSUE, Observatoire Océanologique, 06230 Villefranche sur mer, France and which has been named ZOOSCAN. This system allows a direct, rapid, exhaustive, non-destructive enumeration and measurement of biological liquid samples such as biological liquid preparations, marine or (under)ground water samplings and containing organisms whose are small plants or animals such as microplankton, mesozooplankton and micronekton.

Thanks to the system, a given sample is optically digitized/scanned as to produce an image, the objects within the image are automatically detected, their outlines visualized and labeled. The variability of the analysis of the organisms is reduced compared to traditional human analysis of samples.

The time required to digitize and analyze images has always been a critical aspect limiting the actual use of automated digital imaging systems for massive zooplankton analysis. One of the major attributes of the system of the invention is rapid sample processing. Digitization and analysis of a complete sample containing 1500-2000 individuals requires less than 15 minutes. Coincident task processing (identification of the previous sample during the digitization of the following one) may further reduce the duration time of the analysis. As a consequence, and depending of the number of samples, the results are obtained in seconds or minutes as compared to hours or days with traditional methods.

Moreover, there is no more need to keep the sample for further analysis, which requires chemical fixation of the sample with formol (toxicity), as it is possible to later retrieve an image of a given sample and to work directly on said image. The organisms analyzed are in their natural state and environment, albeit reduced in the size of a sample, when the scanning is done and this avoids possible bias due to sample preparation. In addition to raw living organisms, anesthetized living organism can be analyzed thanks to the non-destructive nature of the proposed device. Samples from sediment traps or the meiobenthos (zooplankton size benthic organisms) can also be analyzed.

Thanks to the system including an optical scanning device connected to a computer with a program, it is possible to display at will images of the samples, part (selection) of images and notably the organisms and to make calculations on the selections or the image as a whole, notably, as to gain morphological information about the organisms. Moreover, storage and retrieving tolls are available for the images, selections and/or calculations, including the entry of contextual information as to easily identify images, selections and calculations. Generic graphical algorithms readily available in modern computers may be used with benefit.

The optical scanning device uses for the scanning part, techniques which are readily available at low cost such as mobile scanning linear optical sensor which are found in table scanners, facsimile apparatus or digital copiers. It is even possible to use a modified and/or commercialized table scanner for building the optical scanning device of the invention.

BRIEF DESCRIPTION OP THE DRAWINGS

Figure 2:
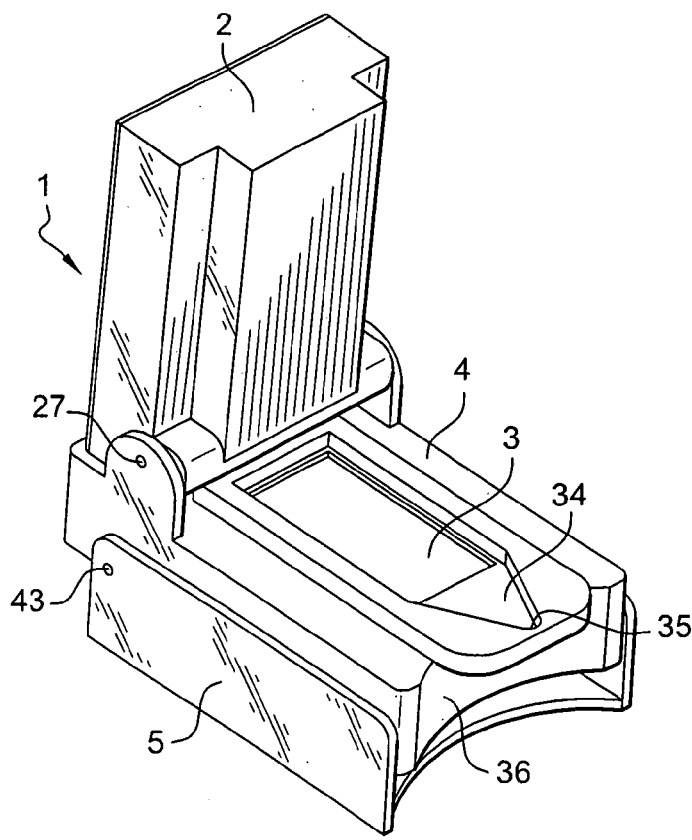
Figure 3:
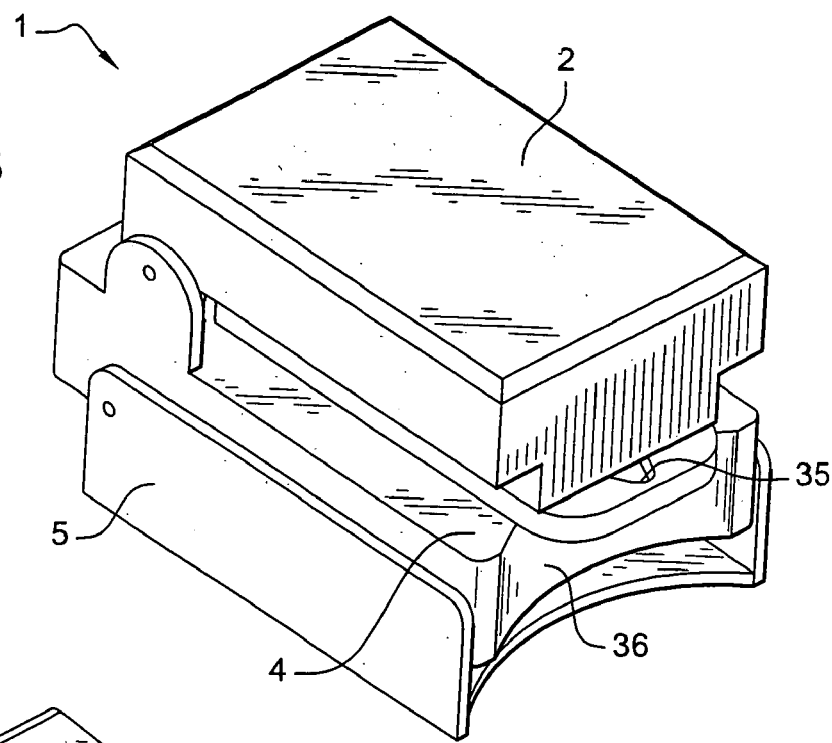
Figure 4:
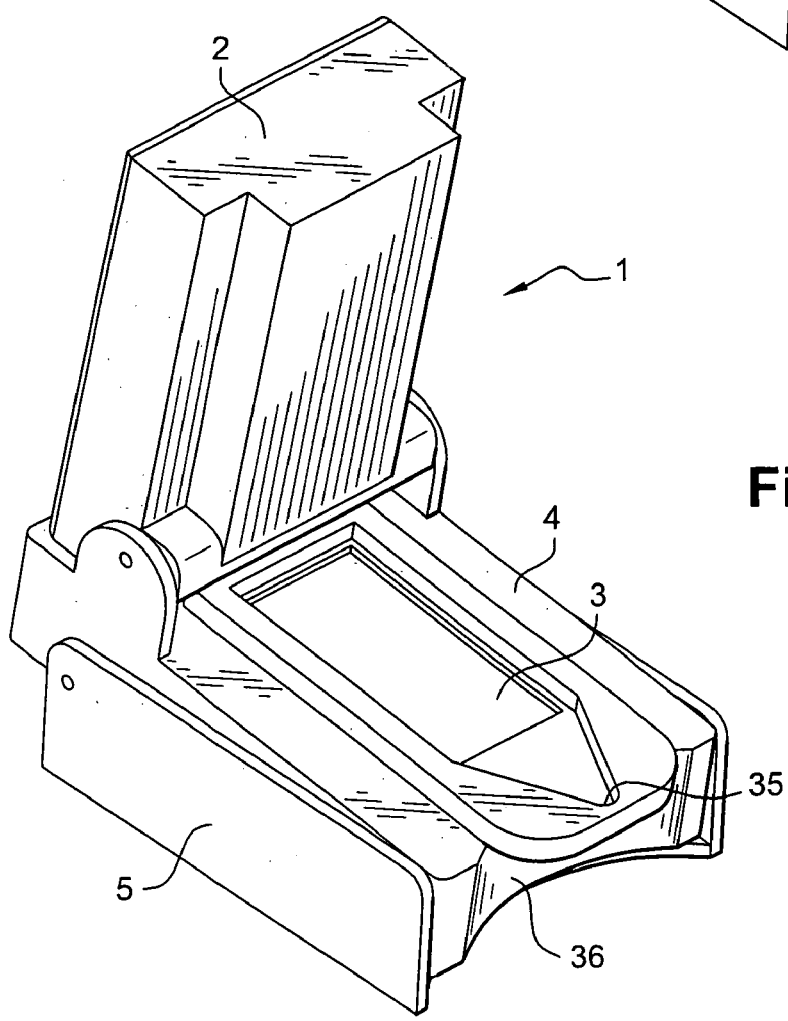
Figure 5:
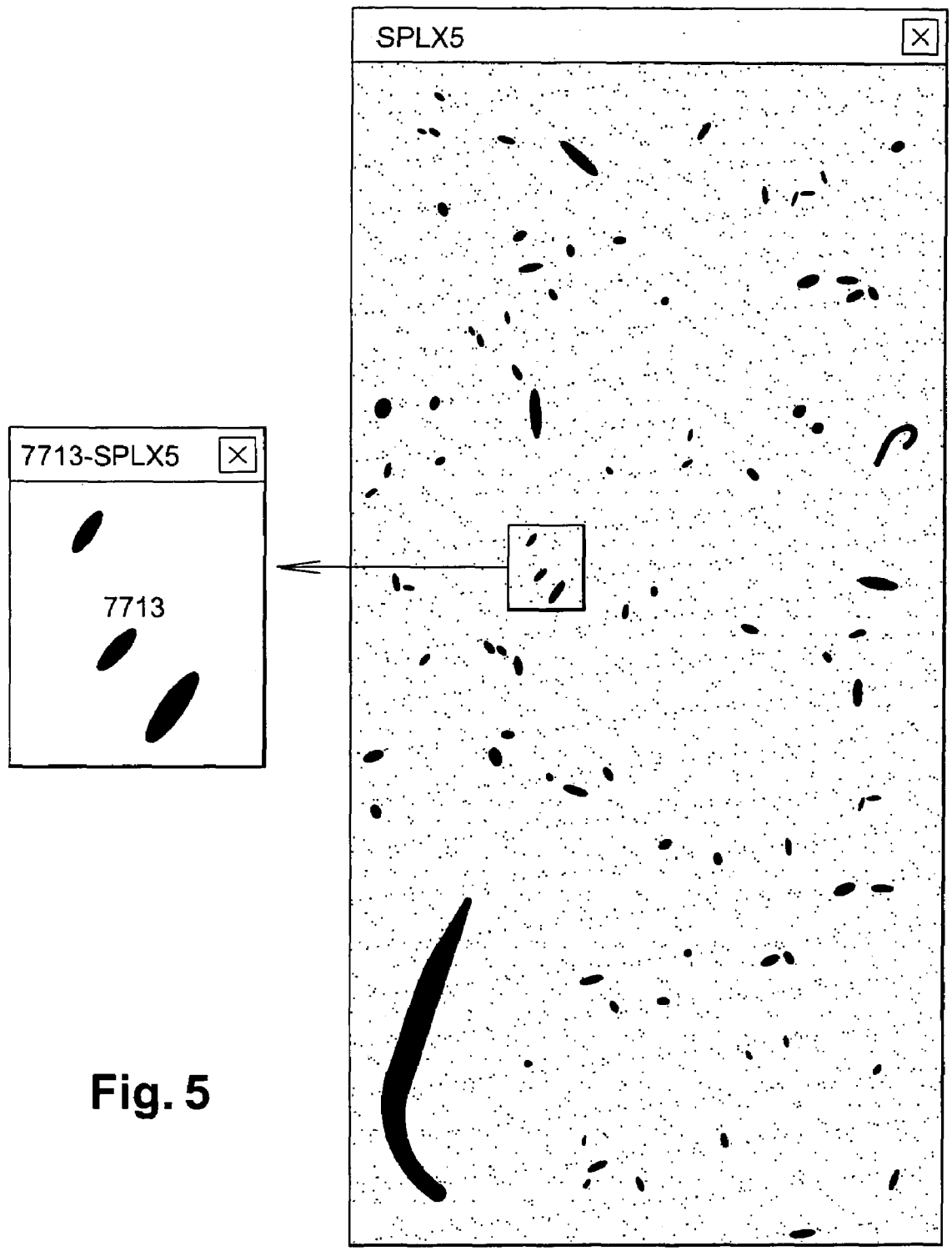
Figure 6:
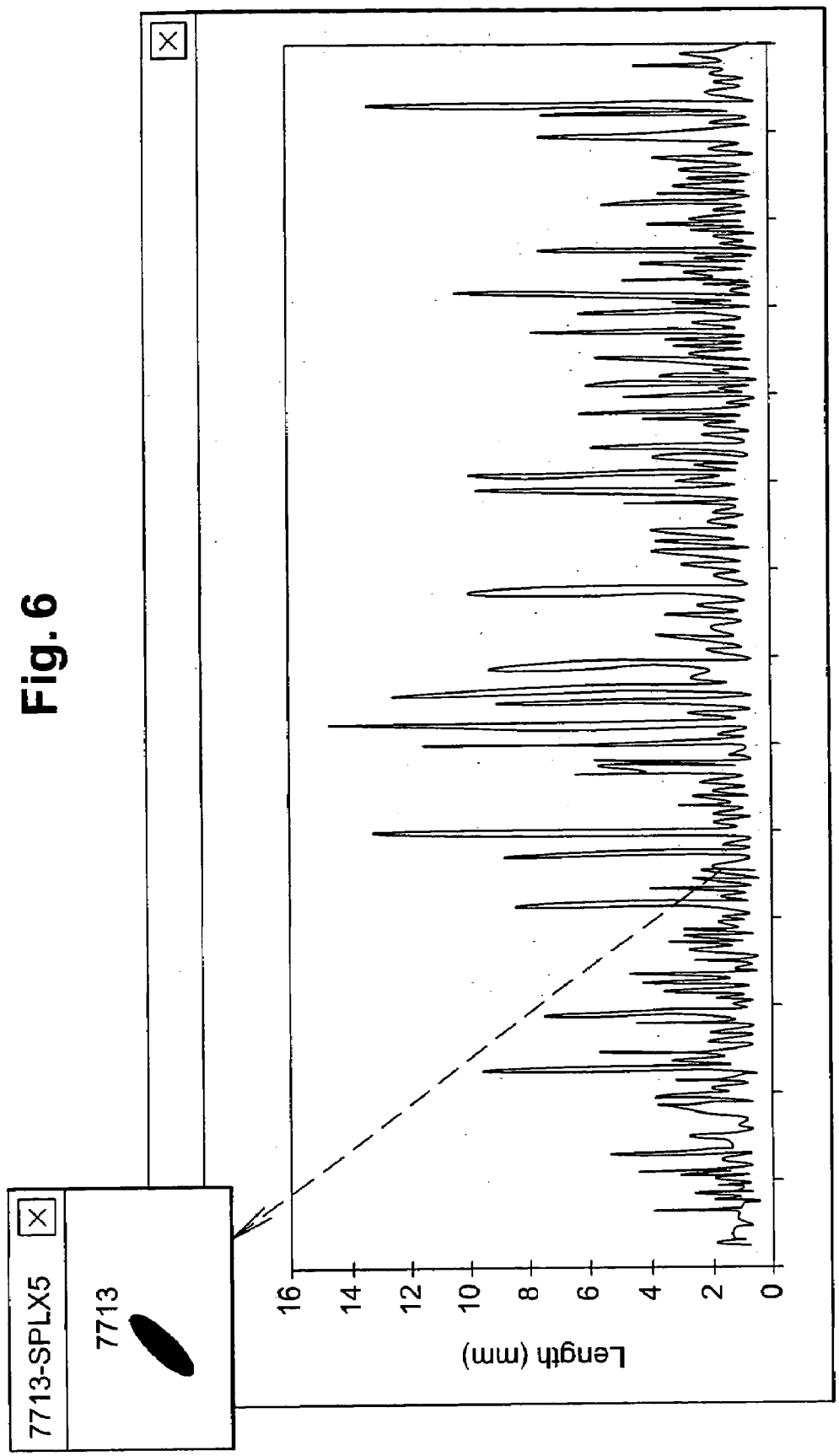
Figure 7:
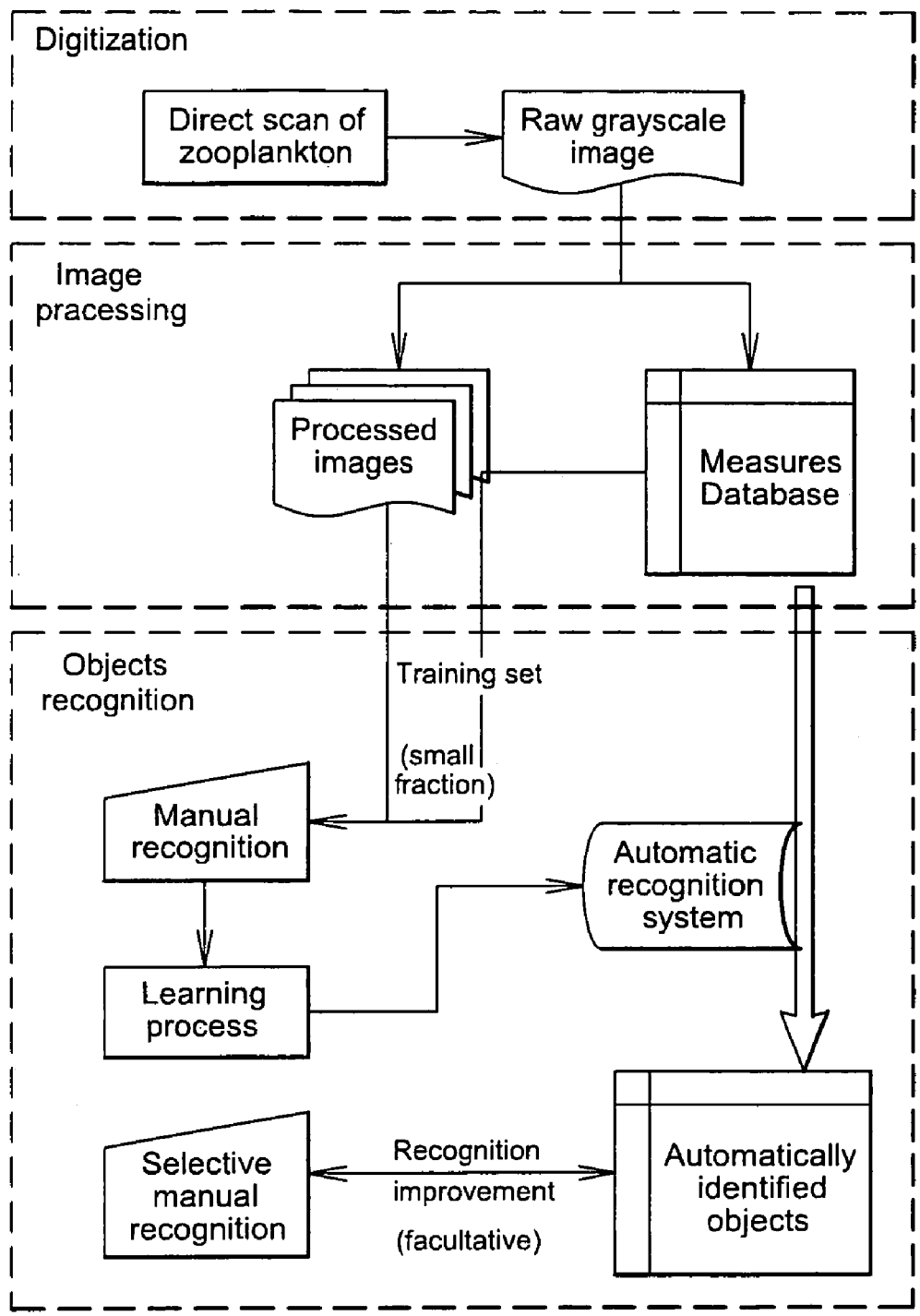
Figure 8:
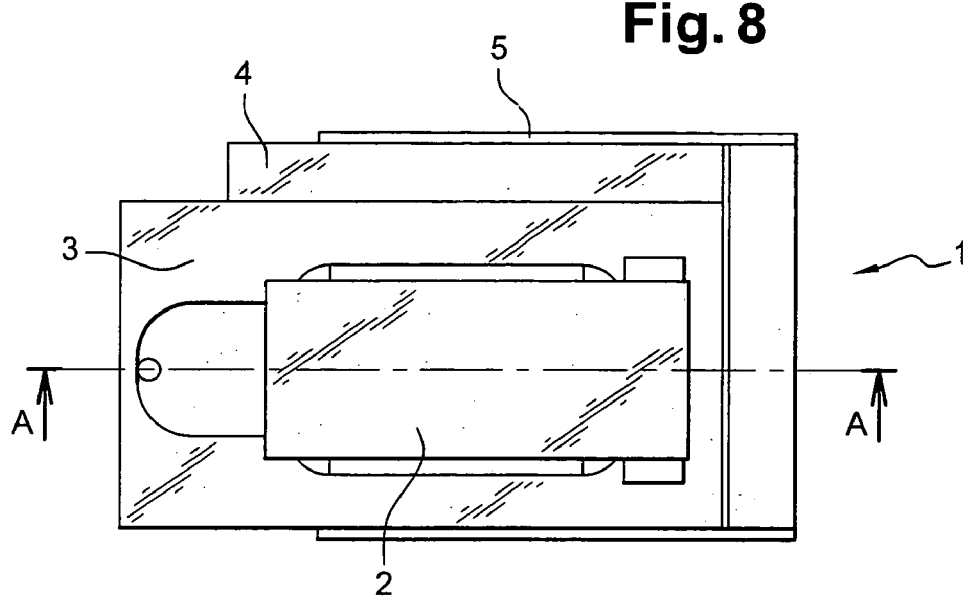
Figure 9:
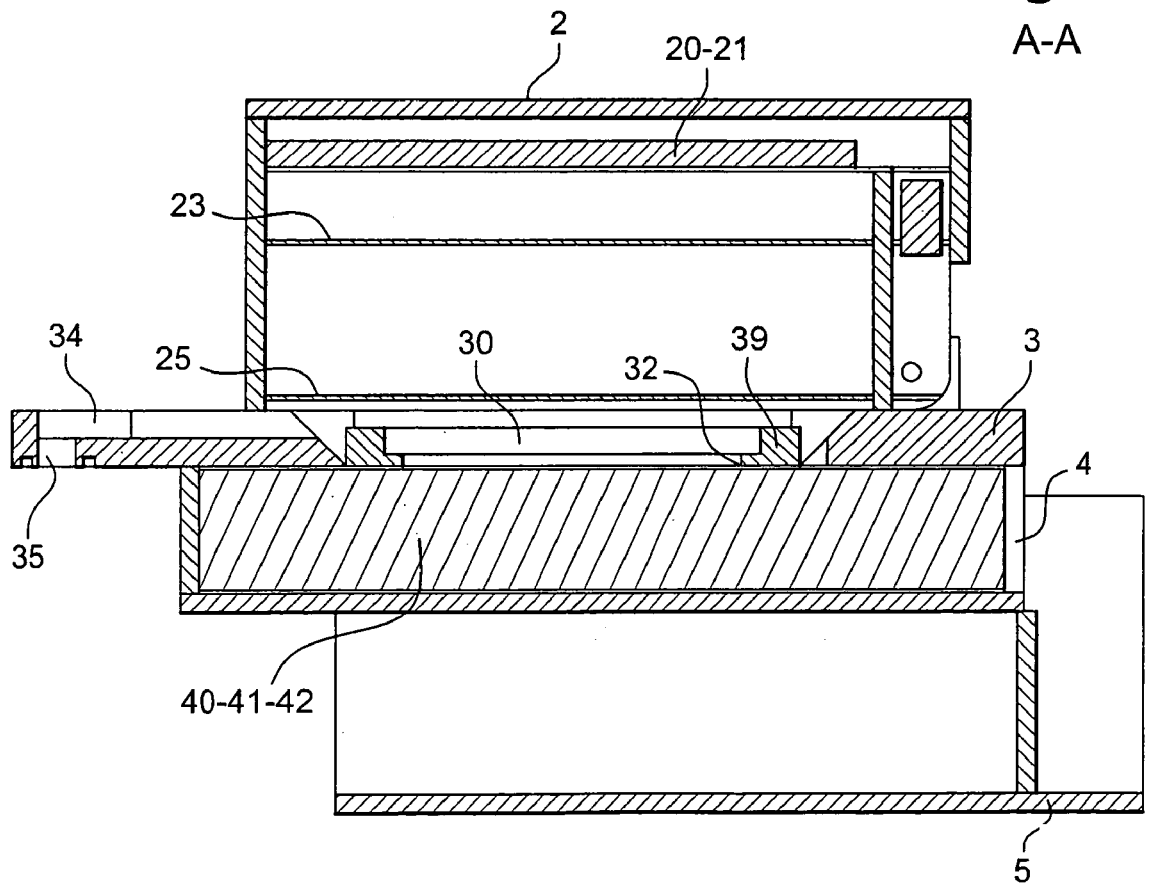
Figure 10:
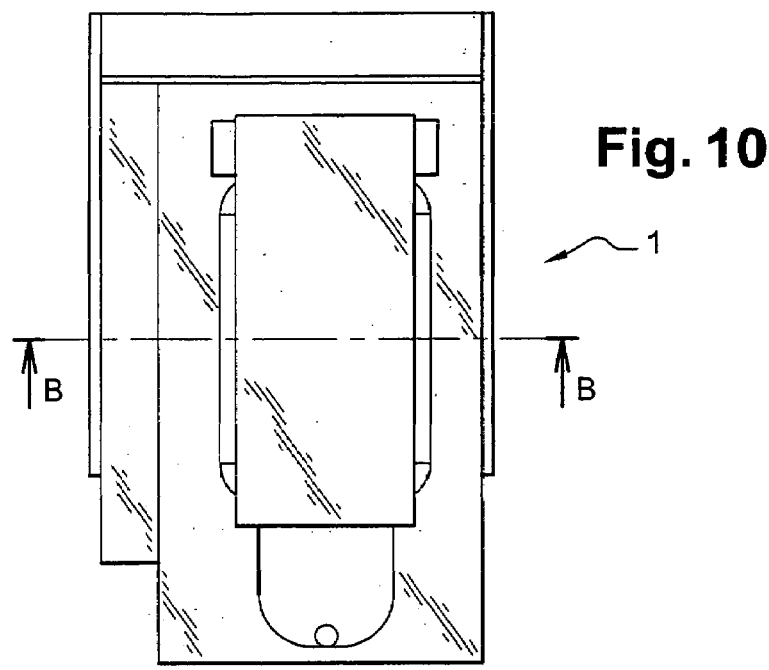
Figure 11:
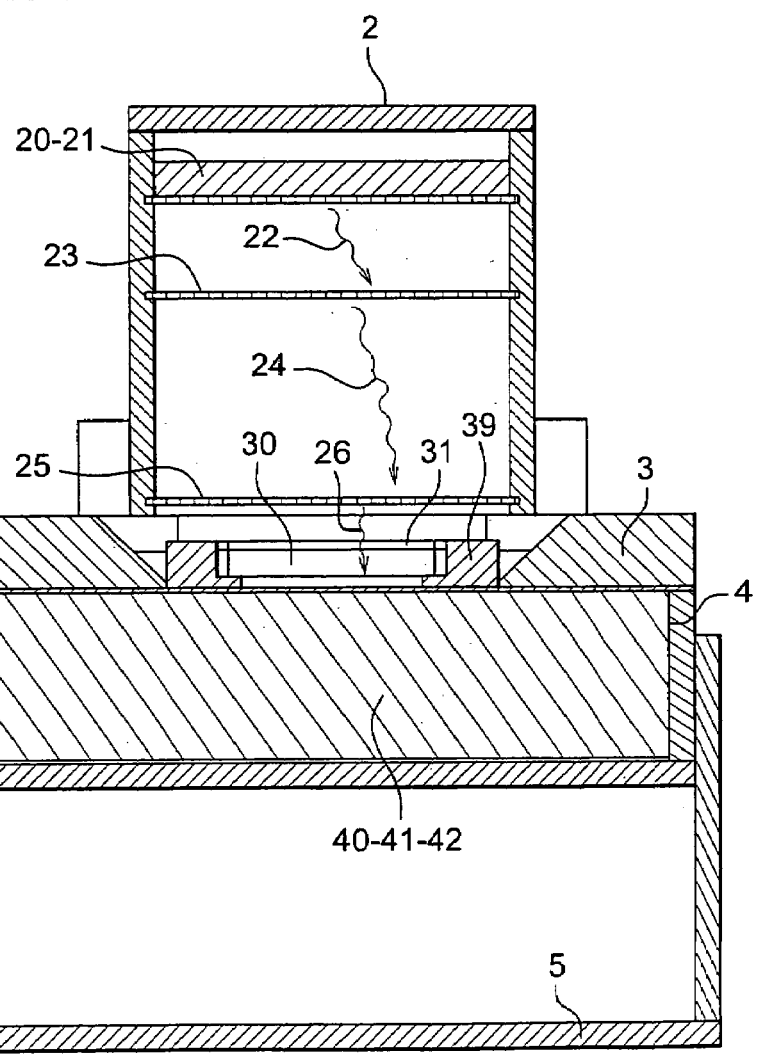

Examples and a preferred embodiment of the invention are now described in relation to:

FIG. 1, which is a schematic view of a vertical plane median section of the optical scanning device of the invention, FIG. 2, which is a perspective view of the optical scanning device of the invention in a preparation phase, FIG. 3, which is a perspective view of the optical scanning device of the invention in a scanning phase, FIG. 4, which is a perspective view of the optical scanning device of the invention in a flushing phase, FIG. 5, which is an image produced by the optical scanning device of the invention and of a zoomed selection of the image, FIG. 6, which is an example of a graph representation resulting of an image analysis and of the selection of an object within the graph, FIG. 7, which is a flowchart of the process of operation of a computerized system using the device of the invention, FIG. 8, which is a top view of a second embodiment of the invention with indication of the section plane A-A of the representation of FIG. 9, FIG. 10, which is a top view of a second embodiment of the invention with indication of the section plane B-B of the representation of FIG. 11.

DESCRIPTION OF THE PREFERRED EMBODIMENTS

A first embodiment of the optical scanning device is now described in relation to FIG. 1. This optical scanning device 1 is made of three main parts whose are: a tank 3 optically enclosed between an upper illumination assembly 2 and a lower optical sensing assembly 4. The tank is optically enclosed because no external light ray may reach the sample or the optical sensing assembly. The tank is part (joint) of to the optical sensing assembly and is open on top, the sample 30 being retained between a transparent bottom wall 32 made of glass and four peripheral walls, the tank being rectangular in shape, a free sample surface 31 being on top. The illumination assembly is flappable over the optical sensing assembly as to gain access to the tank in an open position of the optical scanning device 1.

The optical scanning device is put on a resting surface (for example a laboratory table) in a way as to have an equal thickness of sample over the scanning area. This may be achieved by construction and using a resting surface that is horizontal and/or by adjustable feet under the device and which are adjusted in order to have the sample surface equally disposed from marks (or the top) of the peripheral walls.

The optical sensing assembly has a moving part able to move in a plane parallel to the sample as to scan an area of the sample of sensibly equal thickness. On FIG. 1, the moving part of the optical sensing assembly is an optical sensor 42 which is a linear sensor having a plurality of unitary optical transducers disposed along a sensing line in the plane. The optical sensor is movable in a direction perpendicular to the sensing line in the plane as to scan the area and produce a two-dimension (2D) image of the sample. In this configuration, device closed for scanning, the plane, the bottom tank wall 32 and the sample surface 31, are parallel plane surfaces. In addition, a black bottom 41 is provided at the bottom of the optical sensing assembly and a lateral (to the scanning area) illumination with bottom fluorescent tubes 40 which may provide an even illumination. The relative position of the optical sensor to the sample is defined as to have a focused image of the sample.

The illumination assembly 2 provides a luminous source sensibly homogeneous in the scanned area and it includes towards the sample, an optical grid filter 25 with a surface parallel to the plane and transmitting only light rays sensibly perpendicular to its surface. This filter is a 3M® optical filter of the type used on computer screens as to avoid glare and limiting lateral eyes dropping. Thanks to this filter 25, the light rays 26 reaching the sample are sensibly perpendicular to the sample surface 31. The luminous source also includes in the illumination assembly 2: lateral fluorescent tubes 20 emitting light rays towards a luminescent plastic plate 21 disposed parallel to the plane. The light rays re-emitted 22 by the luminescent plastic plate 21 towards the sample are passing through a frosted glass plate 23 parallel to the plane before being 24 filtered by the optical grid filter 25 and then reaching the sample surface 31.

During scanning it is possible to illuminate the sample only with the illumination assembly, that is from the top, or only from the optical sensing assembly, that is from the bottom, or by both assemblies, that is from top and from bottom, as to be able to have a transmission or a reflection image (or a mix). If the illumination is dimmable, the ratio of illumination from top and/or bottom can be controlled on purpose.

It is also possible to use as a luminous source in the illumination assembly 2, an OSRAM® PLANON® lamp which is a flat light source with uniform output and which can replace the lateral fluorescent tubes and their associated optical elements, notably the luminescent and frosted plates and, eventually, the filter in the illumination assembly. Such lamp may also be used for the lighting assembly of the optical sensing assembly.

The liquid or humid sample is contained in a tank having a bottom wall that is transparent and peripheral walls (four on the figures as the tank is rectangular shaped) and, in addition for a closed tank (not represented), an upper wall that is also transparent. The peripheral walls have a height such as to avoid the spilling of the sample when the open tank is in horizontal position, that is, the thickness of the sample in horizontal position is never made greater than the height of the peripheral walls, and preferably, lower than the bottom of a gutter in a peripheral wall which act as an over-fill security if too much sample is introduced in the tank.

Preferably, the sample tank is configured as to avoid artifacts due to possible meniscus in the scanning area along the peripheral walls thanks to stepped 33 peripheral walls which steps are overstepped by the sample, the sample surface overflooding said step. Preferably, the steps of the peripheral walls are transparent (altuglas®) and the remaining of the peripheral walls may be opaque. This allows taking into account in the image, objects which could be attached (attracted) by the walls. However, in other embodiments, the peripheral walls may be made completely opaque or completely transparent, depending of the researched effect on the image. The steps can be made integral of the peripheral walls as on FIG. 1 or can be made independent as shown in relation to FIGS. 8 to 11.

The optical scanning device has an optical resolution of approximately 10 μm, that is a pixel of the image corresponds to an area of the sample of about 10 μm side. The size of the scanned area of the sample tank depends of the optical and mechanical characteristics of the optical sensing assembly and can be made to be as large as A3 size or even larger. In case regular A4 optical scanner is used for the construction of the device, the tank area is of that order of size.

FIGS. 2, 3 and 4 are related to the operation of the device of FIG. 1. As to ease the operation and specifically the flushing (evacuation) phase for emptying the tank, the optical scanning device 1 has a support or rest 5 that is disposed on a working surface, for instance a laboratory table.

On FIG. 2, for the preparation phase, the optical scanning device is in an open state where the tank is made accessible and can be filled-in by an operator. The tank 3 is sensibly horizontal in this state. The illumination assembly 2 has been flipped around a hinge axis 27 located at the rear of the device. The hinge is arranged between the illumination assembly 2 and the optical sensing assembly 4 but it could have been arranged between the illumination assembly 2 and the support 5. A retaining mechanism may be used to limit the movement and/or to avoid an accidental or brutal closure of the device. On one of the peripheral walls of the sample tank 3, a gutter 34 can be seen ending with an outlet 35 opening on a free bottom face part of the peripheral wall in a sample recover space 36, where the sample in the flushing phase (FIG. 4) can be collected.

On FIG. 3, for the scanning phase, the optical scanning device is in a closed state where the tank is protected from external light rays. It is then possible to start scanning for producing data of the image of the sample, the data being sent to an external computer for storage and/or display and/or processing.

On FIG. 4, for the flushing phase, the optical scanning device is in an open state and the optical sensing assembly tilted in order to have the tank inclined and drained through a gutter 34 arranged in the lowest (when inclined) peripheral wall, practically in the peripheral wall opposed to the hinge which allows the tilting of the optical sensing assembly. An outlet 35 is provided at the end of the gutter. The hinge axis 43 is arranged between the optical sensing assembly 4 and the support 5. A retaining mechanism may be used to limit the movement and/or to avoid an accidental or brutal tilting of the optical sensing assembly and/or also to lock it when the illumination assembly is being tilted for opening the device 1, a catch or stop toward the top is sufficient. An interlocking mechanism is preferably disposed between the illumination assembly 2 and the optical sensing assembly 4 as to avoid the tilting of the optical sensing assembly 4 when the device is closed and, eventually, to avoid the tilting of the illumination assembly 2 for closure when the tank is inclined.

Many variations of the optical scanning device are available:

The illumination assembly can be under the tank and the optical sensing above. The tank can be closed and completely filed-up with the sample (inlet and outlet are thus needed for filing and emptying) and there is no more constraint on the horizontality of the free sample surface. This means that the device can be used in any position (or in mobile environment such as sea). Note that, in moving conditions, such as board on a ship, a device with an open tank can be used if the sample is put in a high-density viscous medium.

Moreover, due to the inlet and outlet that could be connected to pipes, there is no more need for opening and closing the device as to gain access to the tank. Note that this would also be possible in the case of an open tank if inlet and outlet were provided. With the port(s) for the tank, it could also be possible to suppress the inclination of the tank in the flushing phase thanks to an aspiration pump but with the difficulty of completely emptying the tank in some positions.

itself or a derivative of the image (variation). Other patters form recognition sub-process may be used.

Various attributes, mostly dimensional attributes, are extracted from the images by calculation for each object selected in the image using functions available in commercially available program Libraries and/or made on purpose. Images (or selections in the images) are saved and stored in compressed form for further reference. Results of attributes calculation are tabulated, possibly graphed, and may be stored. The following table is an example of such a table of attributes for objects of a given image sample:

| Sample | Date | Label | Area | Length | Wh | DiaMm | DiaMx | Perim | PerCnv | Elng | Cpt | PixSum |
|---|---|---|---|---|---|---|---|---|---|---|---|---|
| B011114 D03 | Nov. 14, 2001 | 7568 | 135737 | 1359 | 100 | 335 | 1078 | 2917 | 2414 | 14 | 5 | 92210 |
| | | 7585 | 151131 | 1155 | 131 | 362 | 767 | 2572 | 1912 | 9 | 3 | 109200 |
| | | 7620 | 211808 | 2002 | 106 | 477 | 1252 | 4216 | 2962 | 19 | 7 | 193500 |
| | | 7634 | 190122 | 918 | 207 | 385 | 813 | 2249 | 2020 | 4 | 2 | 227800 |
| | | 7662 | 99780 | 695 | 144 | 283 | 616 | 1677 | 1474 | 5 | 2 | 83670 |
| | | 7705 | 211808 | 1162 | 182 | 448 | 856 | 2687 | 2081 | 6 | 3 | 249800 |
| | | 7713 | 605872 | 2277 | 142 | 1532 | 1922 | 8838 | 5479 | 20 | 10 | 798700 |

The optical sensing assembly can use other scanning techniques such as a single element sensor but this would take lot of time to get an image or such as a X-Y array sensor but this is costlier. The sensor can be a moving (as in the example of FIG. 1) or not sensor (in the last case, a moving mirror would be used). The optical sensing assembly can use additional optical elements such as magnifier lenses.

As concern the operation of the device, the optical scanning device is connected to a computer which controls its operation and which receives the image data of scans. The computer that is used in connection with the optical scanning device, is preferably of graphical user interface type (for example WINDOWS®, LINUX® . . . ) with graphical tools that may be applied to the image in addition to the specific program of the ZOOSCAN system. With such type of computer, the actions of the operator on the computer may be reduced to simple clicks on a mouse or a button on the optical scanning device or, preferably, automated by detection of the closing/opening of the optical scanning device. This is particularly interesting because the operator has to manipulate liquids which may spill on a keyboard or other electrical parts and which could be detrimental (saline sea water) or dangerous (electrical shock as saline sea water is more conductive). In addition, the illumination (top and bottom) can be automatically switched on only when in scanning phase as to protect the fluorescent tubes.

Preferably, external or accessible parts of the device are made of plastic material and the metallic or electronic parts are protected from possible spills of liquid. The device is preferably earthed and has double isolation.

Beside receiving data from acquisitions of images by scanning (digitization), the computer can process the images. The processing of images can be in real time, that is each time a new image is received, or later in a batch processing. The processing can be described by two main types of operations, the first type for image treatment (for example contrast correction, filtering . . . ) and the second type is the analysis of the image (determination of the objects, i.e. organisms, and then calculation of objects attributes). The determination of the objects is done with data selection thanks to a threshold filter selecting data having particular values as regards certain pixel characteristics such as intensity, level of gray . . . of the image This table stores the flowing fields: Sample referring to the image identification of a sample, Date, Label referring to an object identification, Area, Length, Wh referring to the Width, DiaMn referring to the minimum diameter, DiaMx referring to the maximum diameter, Perim referring to the Perimeter, PerCnv referring to the convex perimeter, Elng referring to the Elongation, Cpt referring to the Compactness and PixSum referring to the number of pixels of the object. It has to be noted that each object is referenced in this table by a label and that there is another table that stores the position of each object (label+position) within said given image sample. Conversely, it could have been possible to store the position directly in the given table.

It is also possible to implement an automated identification process of faunistic groups, using classification techniques like neural networks, random forest and classification trees with bagging.

Preferably, the analysis process is improved by combining the identification methods with error detection techniques. Beside the automated analysis process, a semi-automated technique is also available, allowing for error correction by user visual control. Thumbnail images of each organism are also provided.

In addition to the control of the optical scanning device and the image processing operations, any stock management tools such as bar codes and reader (or even the optical scanning device if an area of the scanning surface can be reserved for the reading of a bar code) may be advantageously used in case multiple samples are analyzed. As an example, stickers may be printed with bar codes coding different sample identifications before a sampling operation for each sample one stickable and one detachable), and when a bottle is filed-up with biological liquid, a sticker (with its detachable part) is sticked on the bottle. Later, when the bottles are used for analysis, the detachable bar code is read with the sample in the optical scanning device. In such a case, a specific bar code reader reads the identification of the sample.

Preferably, in an automatic mode that can be selected by the operator, when an image is scanned and transferred into the computer, predefined processing operations are automatically done. These operations are of two main types, the first type for image treatment (for example contrast correction, filtering . . . ) and the second type is the analysis by itself, in order to determine the objects and then calculate the attributes. For both types, the operations that are done are predefined by the operator in a configuration menu. Some of the operations may be systematically selected or not, that is they will always occur or not occur, or they may depend of conditions related to the current image which is processed, that is the operation will occur or not depending of the image (for example a contrast correction is done only if the variance of gray level of the whole image is too low or too high).

The operator can also switch to a manual mode in which each or parts of the operations are manually selected for each image. In manual mode, when an image is displayed, the objects are not necessarily defined and the attributes calculated. As a consequence and preferably, when the operator click on the image, the analysis of the image (or of the clicked area of the image) is started as to have the objects and their attributes.

In a preferred operational way, the computer displays the received scanned images and the operator is then able to verify visually the quality of the image and accept it or not. Automated tools can also be used to detect noise or possible artifacts and warn the operator when a threshold is reached. A simple detection function is the ratio of clear to dark pixels in the image or the number of objects.

In addition to the image of the sample which can be displayed in a window on the screen of the computer (and possibly printed), the user can visualize a specific object in a specific window in the form of a vignette by clicking for selection on said given object of the image. This is the case on FIG. 5, where in a first window the image is displayed and in a second window, the vignette of the chosen object is displayed. In this example the object, an organism, is referenced by the numerical label 7713. The characteristics of the vignette (size, shape . . . ) can be predefined for example as to depend of the length of the object. The displayed vignette can be copied/pasted and possibly printed or mailed through INTERNET. In addition, when a specific object is clicked, an attribute window may appear on the screen for displaying the calculated attributes related to the said object.

Contextual menus may also be called with the second button of the mouse (menu button usually right of the main button used for selection). Outside an object the contextual menu is a reduced menu (print, copy . . . image treatment: luminosity, contrast, filter . . . ) and on an object the contextual menu gives access to attributes of the object (in full or part), to image treatment (luminosity, contrast, filter . . . ) and to usual tools (print, copy . . . ).

FIG. 6, a plankton tow size distribution is represented with the lengths of the objects on the vertical axis and the identification of the object with a label number on the horizontal axis. This distribution is displayed as a window on the screen of the computer and by clicking on the distribution, the object corresponding to the label at the point of clicking is displayed as a window in a vignette on the screen. In this example, the label is number 7713 and this is an organism which can be classified as a male *Centropages typicus*. The label number allows retrieval of the position of the object within the image and the size of the vignette may be determined, in the simplest way, by the length corresponding to the label in the distribution or, in more sophisticated ways, to other calculated attributes of the object (for example maximum diameter) which may be available in the computer data base.

The ZOOSCAN provides means to develop image databanks. The high resolution of the images, 16-bits grayscale and 2400 dpi and each pixel about 10 microns wide for the images of FIGS. 5 and 6 (other values may be selected), allows specialists to identify fauna to genera or species on images. Non-specialized personnel can use ZOOSCAN for more general categorizations. This method may contribute to the constitution of homogenous datasets from retrospective and future time series analyses. It is also possible to give access to the images to the scientific community through the Internet and undertake investigations in quasi-real time wherever in the world.

On FIG. 7, an example of advanced process of operation of a computerized system using the device of the invention is given in the form of a flowchart. In this specific example, the data of the images is handled in three main operational parts: firstly digitization of an image of a sample by direct scan of zooplankton which gives a raw grayscale image, this is done in the optical scanning device, secondly, image processing in which the images are processed and stored and measurements done, this is done in the computer which is connected to the device, and, thirdly, objects recognition also in the computer. Object recognition is automated in this example thank to a learning method with manual recognition of a training set and comparison with measures in order to determine rules of recognition which are the used for the automatic recognition process. In addition, the automatically identified objects can be, eventually, crosschecked by a human operator through a selective manual recognition for improving the recognition if necessary and/or checking the quality of the automatic recognition.

A second embodiment of the device of the invention is now given in relation to FIGS. 8, 9, 10 and 11. The main difference with the previously described device of FIG. 1 is that the peripheral walls 3 and the steps are independent elements, the steps being in the form of transparent stepped walls 39.

FIG. 8, the device 1 is seen from above in a closed position. A top box or illumination assembly 2 is first seen and, farther, the sample tank 3 with its peripheral walls, then an imaging and lighting box (optical sensing assembly) 4 and finally, a support 5.

FIG. 9 is a lateral cross section along A-A plane of the device 1 of FIG. 8. From top to bottom, one can see the top box 2, the open sample tank 3 and its walls (bottom 32 and peripherals) with transparent stepped walls 39 disposed inside the tank, then the imaging and lighting box 4 and, finally, the support 5. The top box 2, which is the illumination assembly, contains a light source with fluorescent tubes (20 not represented on FIG. 9) and a luminescent plate 21, a frosted plate 23 made of glass and an optical filter 25 from 3M® as previously described. The tank 3 with its walls is containing the sample 30. One of the peripheral walls has a gutter 34 and an outlet 35. The imaging and lighting box 4, which is the optical sensing assembly, contains (not represented in detail on FIG. 9) an optical sensor 42, a black bottom 41 and a lighting source 40.

FIG. 10, the same device 1 as on FIG. 8 is seen from above in a closed position.

FIG. 11 is a frontal cross section along B-B plane of the device 1 of FIG. 10. Again, from top to bottom, one can see the top box 2, the open sample tank 3 and its walls (bottom 32 and peripherals) with transparent stepped walls 39 disposed inside the tank, then the imaging and lighting box 4 and, finally, the support 5. The top box 2, which is the illumination assembly, contains a light source with fluorescent tubes (20 not represented on FIG. 9) and a luminescent plate 21, a frosted plate 23 made of glass and an optical filter 25 from 3M® as previously described. The light rays 22 emerging from the luminescent plate reach the frosted plate 23. The light rays 24 emerging from the frosted plate 23 reach the optical filter 25. Finally, the light rays 26 emerging from the filter 25 reach the sample 30 in the tank 3. The imaging and lighting box 4, which is the optical sensing assembly, contains (not represented in detail on FIG. 9) an optical sensor 42, a black bottom 41 and a lighting source 40.

Beside numerous variations already listed many variations with the scope of the invention may be implemented in the optical scanning device and associated computer program. For example, the illumination of the sample can be made of or include specific length waves interacting with biological matter. In such instance, ultraviolet or colored light rays may be used to analyze the sample.

The invention claimed is:

1. Optical scanning device (1) for the production of a 2D computer image of an illuminated liquid or humid biological sample observed by transparency, characterized in that
an even thickness of the liquid biological sample (30) is disposed in a tank (3) optically enclosed between an illumination assembly (2) and an optical sensing assembly (4),
the optical sensing assembly having a moving part able to move in a plane parallel to the sample as to scan an area of the sample of sensibly equal thickness,
the illumination assembly having a luminous source sensibly homogeneous in the scanned area and including towards the sample, an optical grid filter (25) with a surface parallel to the plane and transmitting only light rays sensibly perpendicular to its surface.

2. Optical scanning device according to claim 1, characterized in that the biological sample can, in addition, be observed by reflection and that the optical sensing assembly has, in addition, opposite to the sample as regard the moving part, a black end (41) and a lighting assembly, as to allow illumination of the sample from the illumination assembly or from the optical sensing assembly or from both.

3. Optical scanning device according to claim 2, characterized in that the lighting assembly of the optical sensing assembly has lateral stationary fluorescent tubes (40).

4. Optical scanning device according to claim 2, characterized in that the lighting assembly of the optical sensing assembly has a moving fluorescent tube attached to the moving part of the optical sensing assembly.

5. Optical scanning device according to claim 2, characterized in that the illumination assembly (2) is under the sample tank (3) and the optical sensing assembly (4) is above the sample tank, said sample tank being an open chamber joint to the illumination assembly and having peripheral walls and a transparent bottom wall (32) parallel to the plane which is horizontal, and in that the optical sensing assembly is tiltable along one of its edge as to open the device and gain access to the sample tank and, conversely, to close it.

6. Optical scanning device according to claim 2, characterized in that the illumination assembly (2) is above the sample tank (3) and the optical sensing assembly (4) is under the sample tank, said sample tank being an open chamber joint to the optical sensing assembly and having peripheral walls and a transparent bottom wall (32) parallel to the plane which is horizontal, and in that the illumination assembly is liltable along one of its edge as to open the device and gain access to the sample tank and, conversely, to close it.

7. Optical scanning device according to claim 6, characterized in that the optical sensing assembly is tiltably supported by a support (5) as to incline the plane from a position where it is horizontal, to a position where it is inclined as to drain the sample tank and, conversely, to return to an horizontal position of the plane.

8. Optical scanning device according to claim 7, characterized in that the illumination assembly and the optical sensing assembly are interlocked as to allow the draining of the sample tank only when the device is open.

9. Process of operation of an optical scanning device (1) for the production of a 2D computer image of an illuminated liquid or humid biological sample observed by transparency or by reflection, characterized in that an optical scanning device according to claim 7 is used and in that:
in a preparation phase, the device being open, a sample is introduced in the tank,
in a scanning phase, the device being closed, the sample is scanned as to produce data corresponding to an image of the sample,
in a flushing phase, the device being open, the optical sensing assembly is tilted as to drain the sample tank.

10. Process of operation according no claim 9, characterized in that during the scanning phase, in order to illuminate the liquid or humid biological sample, either or both the luminous source of the illumination assembly and the lighting assembly of the optical sensing assembly are switched on.

11. Process of operation according to claim 9, characterized in that it has an additional phase in which objects are selected in an initial image and that the initial image minus the objects is subtracted from the initial image as to keep only the objects in an object image.

12. Optical scanning device according to claim 1, characterized in that the luminous source of the illumination assembly is a flat lamp disposed above the tank.

13. Optical scanning device according to claim 1, characterized in that the luminous source of the illumination assembly includes a source (20) of light rays emitting light rays towards a luminescent plate (21) disposed parallel to the plane, light rays re-emitted (22) by the luminescent plate towards the sample passing through a frosted plate (23) parallel to the plane before being (24) filtered by the optical grid filter (25) and then reaching the sample (30).

14. Optical scanning device according to claim 1, characterized in that the moving part of the optical sensing assembly is an optical sensor which is a single optical transducer movable along two perpendicular directions in the plane as to scan the area.

15. Optical scanning device according to claim 1, characterized in that the moving part of the optical sensing assembly is an optical sensor (42) which is a linear sensor having a plurality of unitary optical transducers disposed along a sensing line, the optical sensor being movable in a direction perpendicular to the sensing line in the plane as to scan the area.

16. Optical scanning device according to claim 1, characterized in that the moving part of the optical sensing assembly is a linear mirror disposed along a mirror line, the linear mirror being movable in a direction perpendicular to the mirror line in the plane as to scan the area and reflecting said area to a fixed optical sensor.

17. Optical scanning device according to claim characterized in that the sample tank is a closed chamber having at least one port, two opposite walls parallel to the plane and peripheral walls, at least said two opposite walls being transparent.

18. Optical scanning device according to claim 1, characterized in that the sample tank is an open chamber with a sample free surface (31) and having a bottom wall (32) parallel to the plane and peripheral walls, at least said bottom wall being transparent.

19. Optical scanning device according to claim 18, characterized in that the peripheral walls are stepped (33) (39) by mean of a transparent material to allow the sample to overstep said step in order to avoid a possible meniscus in the image area.

20. Optical scanning device according to claim 19, characterized in that at least one of the peripheral walls has a gutter.

21. Optical scanning device according to claim 1, characterized in that the optical scanning device has a magnifier as to have an image of the sample which is enlarged.

* * * * *